(12) United States Patent
Minakuchi

(10) Patent No.: US 9,890,191 B2
(45) Date of Patent: Feb. 13, 2018

(54) MIXED-MODE ANTIBODY AFFINITY SEPARATION MATRIX AND PURIFICATION METHOD USING THE SAME, AND THE TARGET MOLECULES

(71) Applicant: Kaneka Corporation, Osaka-shi, Osaka (JP)

(72) Inventor: Kazunobu Minakuchi, Takasago (JP)

(73) Assignee: KANEKA CORPORATION, Osaka (JP)

(*) Notice: Subject to any disclaimer, the term of this patent is extended or adjusted under 35 U.S.C. 154(b) by 247 days.

(21) Appl. No.: 14/424,718

(22) PCT Filed: Aug. 19, 2013

(86) PCT No.: PCT/JP2013/072065
§ 371 (c)(1),
(2) Date: Feb. 27, 2015

(87) PCT Pub. No.: WO2014/034457
PCT Pub. Date: Mar. 6, 2014

(65) Prior Publication Data
US 2015/0225445 A1 Aug. 13, 2015

(30) Foreign Application Priority Data

Sep. 3, 2012 (JP) ................. 2012-193069

(51) Int. Cl.
| | | |
|---|---|---|
| C07K 1/16 | (2006.01) | |
| C07K 1/18 | (2006.01) | |
| C07K 1/22 | (2006.01) | |
| B01J 39/26 | (2006.01) | |
| C07K 16/00 | (2006.01) | |

(52) U.S. Cl.
CPC ............. *C07K 1/165* (2013.01); *B01J 39/26* (2013.01); *C07K 16/00* (2013.01); *C07K 1/18* (2013.01); *C07K 1/22* (2013.01)

(58) Field of Classification Search
None
See application file for complete search history.

(56) References Cited

U.S. PATENT DOCUMENTS

| | | |
|---|---|---|
| 3,932,557 A | 1/1976 | Matthews |
| 4,210,723 A | 7/1980 | Dorman et al. |
| 4,772,653 A | 9/1988 | McKenna |
| 5,250,613 A | 10/1993 | Bergstrom et al. |
| 5,260,373 A | 11/1993 | Profy et al. |
| 5,874,165 A | 2/1999 | Drumheller |
| 6,399,750 B1 | 6/2002 | Johansson |
| 8,101,425 B1 | 1/2012 | Carbonell |
| 2005/0143566 A1 | 6/2005 | Hober |
| 2006/0160064 A1 | 7/2006 | Carbonell |
| 2006/0194950 A1 | 8/2006 | Hober et al. |
| 2006/0194955 A1 | 8/2006 | Hober et al. |
| 2007/0112178 A1 | 5/2007 | Johansson et al. |
| 2007/0167613 A1 | 7/2007 | Johansson et al. |
| 2007/0207500 A1 | 9/2007 | Bian et al. |
| 2007/0244307 A1 | 10/2007 | Engstrand et al. |
| 2007/0259453 A1 | 11/2007 | Engstrand et al. |
| 2008/0167450 A1 | 7/2008 | Pan |
| 2008/0177048 A1 | 7/2008 | Gagnon |
| 2009/0171072 A1 | 7/2009 | Alfonso et al. |
| 2009/0247735 A1 | 10/2009 | Gagnon |
| 2009/0270596 A1 | 10/2009 | Gagnon et al. |
| 2010/0022760 A1 | 1/2010 | Hober et al. |
| 2010/0063261 A1 | 3/2010 | Bian et al. |
| 2010/0135987 A1 | 6/2010 | Hickman et al. |
| 2010/0145029 A1 | 6/2010 | Gagnon |
| 2011/0105730 A1 | 5/2011 | Bian et al. |
| 2011/0112276 A1 | 5/2011 | Hober |
| 2011/0118442 A1 | 5/2011 | Engstrand et al. |
| 2011/0139717 A1 | 6/2011 | Malenfant et al. |
| 2011/0144311 A1 | 6/2011 | Chmielowski et al. |
| 2011/0251374 A1 | 10/2011 | Suenaga et al. |
| 2011/0263823 A1 | 10/2011 | Gagnon |
| 2012/0129150 A1 | 5/2012 | Carbonell |
| 2012/0238724 A1 | 9/2012 | Hober |
| 2012/0264915 A1 | 10/2012 | Gagnon et al. |
| 2013/0096276 A1 | 4/2013 | Yoshida et al. |
| 2013/0184438 A1 | 7/2013 | Hober et al. |

(Continued)

FOREIGN PATENT DOCUMENTS

| | | |
|---|---|---|
| EP | 1352957 A1 | 10/2003 |
| JP | 2008-502920 A | 1/2006 |

(Continued)

OTHER PUBLICATIONS

Extended European Search Report dated Dec. 17, 2015 in EP Appln. No. 13833630.0.
Hober et al., "Protein A chromatography for antibody purification", Journal of Chromatography B, 848 (2007) 40-47.
Low et al., "Future of antiboy purification" Journal of Chromatography B, 848 (2007) 48-63.
Roque et al., "Affinity-based methodologies and ligands for antibody purification: Advances and perspectives", Journal of Chromatography A, 1160 (2007) 44-45.
Hermanson et al., "Immobilized Affiity Ligand Techniques", Academic Press 1992, pp. 51-136.

(Continued)

*Primary Examiner* — Daniel E Kolker
*Assistant Examiner* — James L Rogers
(74) *Attorney, Agent, or Firm* — Polsinelli PC

(57) ABSTRACT

A mixed mode antibody affinity separation matrix comprises an antibody affinity ligand and a cation exchange group on a single separation matrix. According to such a matrix in the first step of a process for purifying an antibody or an Fc-containing target molecule, the antibody as the main target substance of the affinity purification can be purified at high purity, the selective separation properties of monomers can also be improved; and the burden on a subsequent impurity removal step can be reduced with respect to the removal of impurities such as aggregates.

4 Claims, No Drawings

(56) References Cited

U.S. PATENT DOCUMENTS

| | | |
|---|---|---|
| 2014/0255423 A1 | 9/2014 | Hickman et al. |
| 2015/0073128 A1 | 3/2015 | Engstrand et al. |

FOREIGN PATENT DOCUMENTS

| | | |
|---|---|---|
| JP | 2008/505851 A | 2/2008 |
| JP | 4391830 B2 | 12/2009 |
| JP | 2010/07583 A | 3/2010 |
| JP | 2010/517942 A | 5/2010 |
| JP | 2010/133733 A | 6/2010 |
| JP | 2010/133734 A | 6/2010 |
| JP | 2011/517462 A | 6/2011 |
| JP | 2011/256176 A | 12/2011 |
| WO | WO-2004/074471 A1 | 9/2004 |
| WO | WO-2005/082483 A1 | 9/2005 |
| WO | WO-2005/082926 A1 | 9/2005 |
| WO | WO-2006/043895 A1 | 4/2006 |
| WO | WO-2008/085988 A1 | 7/2008 |
| WO | WO 2010//019493 A1 | 2/2010 |
| WO | WO-2010/071208 A1 | 6/2010 |
| WO | WO-2010/141039 A1 | 12/2010 |
| WO | WO-2011081898 A1 | 7/2011 |
| WO | WO-2011/118699 A1 | 9/2011 |

OTHER PUBLICATIONS

Ljungquist et al., "Thiol-directed immobilizaton of recombinant IgG-binding receptors", Eur. J. Biochem, 186, 557-561 (1989).

Gagnon et al., "Cooperative multimodal retention of IgG, fragments, and aggregates on Hydroxyapatite", J. Sep. Sci. 2009, 32, 3857-3885.

Pete Gagnon, "Technology trends in antibody purification", Journal of Chromatography A, 1221 (2012) 57-70.

Lackmann et al., "Purification and Structural Analysis of a Murine Chemotactic Cytokine (CP-10) with Sequence Homology to S100 Proteins", Journal of Biological Chemistry, vol. 257, No. 11, Apr. 15, 1992, pp. 7499-7504.

Ion exchange resin and its technology and its application (Basic), Revision 2, Organo Corporation, Mar. 31, 1997, pp. 10,11, 24-27 with its partial translation.

Diaion (R) 1, Revision 4, Mitsubishi Chemical Corporation, H19-10-31, pp. 4, 5, 8, 9 with its partial translation.

MIXED-MODE ANTIBODY AFFINITY SEPARATION MATRIX AND PURIFICATION METHOD USING THE SAME, AND THE TARGET MOLECULES

CROSS REFERENCE TO RELATED APPLICATIONS

This application is a National Phase filing under 35 U.S.C. § 371 of PCT/JP2013/072065filed on Aug. 19, 2013; and this application claims priority to Application No. 2012-193069filed in Japan on Sep. 3, 2012 under 35 U.S.C. §119. The entire contents of each application are hereby incorporated by reference.

TECHNICAL FIELD

The present invention relates to an affinity separation matrix for specifically purifying a target molecule, especially relates to a novel mixed mode antibody affinity separation matrix in which an affinity ligand and another ligand can simultaneously or continuously function on a single matrix, a purification method using the separation matrix, and a target molecule.

BACKGROUND ART

An affinity ligand has a function of specifically binding to a particular molecule, and an affinity separation matrix prepared by immobilizing the ligand to a water-insoluble carrier is utilized for efficient separation and purification of a useful substance from biological components or recombinant cells including microorganisms and mammalians. An industrially utilized antibody affinity ligand includes, for example, a peptide ligand or a protein ligand derived from a microorganism such as protein A, protein G and protein L or consisted of a functional variant (analog substance) obtained by recombinant technology thereof; a recombinant protein ligand such as a camel single strand antibody and an Fc receptor of an antibody; and a chemosynthetic ligand such as a thiazole derivative. The antibody affinity ligand is used in purification of an antibody drug and the like. Since the antibody preparation has lower toxicity and higher specificity than chemicals, there is much demand for an antibody drug as an ideal pharmaceutical.

A monoclonal antibody as active pharmaceutical ingredients of an antibody drug is mainly expressed in a culture fluid as a recombinant protein using a mammalian cultured cell or the like, and purified to a high purity by several steps of chromatography and filtration process before formulation. An antibody drug includes not only a molecule generally called an antibody such as immunoglobulin G and an analog thereof, but also an Fc fusion protein (Fc-containing molecule) in which an Fc region of a constant region of an immunoglobulin molecule is fused to another functional protein or peptide. Antibody drugs are also prepared by purifying and formulating from recombinant microorganisms, secreted substances in the culture supernatant, or expressed substances in bacterial cell or periplasmic space.

Impurities such as aggregates of antibodies (a dimeric and multiple form of a monomer) which are formed or remains in the steps of culture, purification and formulation is a major cause of side effects, and it is an important issue to reduce the impurities on production of an antibody preparation. Here, a monomer is defined as a unit of a molecule of an antibody having a tetramer structure composed of two molecules of heavy chains (H chains) consisting of an Fc region of a constant region, and a variable region, and two molecules of light chains (L chains) consisting of a variable region. A multimer of the unit molecules is regarded as an aggregate, and thought to be a major cause of side effects of an antibody preparation.

Attempts to control suppression of production of the aggregate and remove the aggregate have been made by a complicated management technique and use of an additive in the steps of culture, purification and formulation. Especially, not only suppression of production of the aggregate, but also removal of the aggregate is important in the purification step. Thus, development of a simple and efficient technique for removing the aggregate has been required in the purification step.

Patterning of purification techniques by combining particular unit operations (making of a platform) is developed in the purification step of the antibody preparation. In the early purification step (recovery step), an antibody affinity separation matrix in which protein A is immobilized as a ligand on a water-insoluble carrier (protein A carrier) is widely utilized. A technique of adsorbing an antibody to the protein A carrier under neutral conditions, and eluting the antibody under acidic conditions is generally used. However, in the elution process, the antibody subjected to the acidic conditions tends to be denatured and form an aggregate. In general, impurities such as an aggregate are removed by a combination of ion exchange chromatography, hydrophobic interaction chromatography and the like, in the subsequent step of protein A chromatography step (Non-patent Document 1, Non-patent Document 2, Non-patent Document 3, Patent Document 5).

However, after protein A chromatography step, high content of the aggregate is resulted in lowering of yield of the objective monomeric substance (monomer) in the subsequent step of removing impurities. Thus, not only suppression of formation of an aggregate, but also removal of an aggregate is studied in the protein A chromatography step.

The protein A chromatography step is generally carried out with acidic elution. However, since the lower the elution pH is, the more the risk of formation of an aggregate is, the protein A ligand is modified by means of protein engineering, so that the antibody which requires pH elution as low as about pH 3 can also be eluted near pH 3.5 to 4 (Patent Document 1).

In addition, a method for improving resolution of an aggregate from monomer fraction is examined in the protein A chromatography step. That is to say, optimization of pH and ionic strength at the time of elution, as well as fractionation of the first half of the elution peak and the second half of the elution peak, and the like are proposed. Concretely, there are methods utilizing slight decrease of dissociation constant by contacting an antibody molecule polymerized with a protein A ligand with probability higher than that of an antibody molecule which is not polymerized as a characteristic of the protein A carrier, and utilizing separation mechanisms based on delicate adjustment of hydrophobicity (Patent Document 2, Patent Document 3, Patent Document 4). However, since these methods are difficult to be strictly controlled and have low resolution, these methods are not used as a general separation technique in production of antibody drug.

As described above, although the antibody affinity separation matrix exhibits high specificity to an antibody and is capable of improving the purity, the ability of separating a monomeric substance (monomer) and an aggregate is low even if the usage is strictly set. Thus, the antibody affinity separation matrix had limitation for removing an aggregate.

PRIOR ART

Patent Document

Patent Document 1: JP 4391830
Patent Document 2: WO 2008/085988
Patent Document 3: JP 2010-507583
Patent Document 4: WO 2010/019493
Patent Document 5: WO 2010/141039

Non-Patent Document

Non-Patent Document 1: Hober S. et al., J. Chromatogr. B, 2007, Vol. 848, pages 40-47
Non-Patent Document 2: Low D. et al., J. Chromatogr. B, 2007, Vol. 848, pages 48-63
Non-Patent Document 3: Roque A. C. A. et al., J. Chromatogr. A, 2007, Vol. 1160, pages 44-55

SUMMARY OF THE INVENTION

Problems to be Solved by the Invention

An object of the present invention is to provide a novel separation material which can, in a first chromatography step of a process for purifying an antibody or an Fc-containing target molecule, improve the purity of the antibody as the main target substance of the affinity purification, and can also improve the selective separation properties of monomers, and can reduce the burden on a subsequent impurity removal step with respect to the removal of impurities such as aggregates, and a separation technique thereof.

Solutions to the Problems

As a result of intensive investigation from the viewpoint of the problems, the inventor found that each of an antibody affinity ligand and a cation exchange group (cation exchange ligand) concertedly acts by immobilizing both of the ligands on a water-insoluble carrier, thereby obtaining a separation matrix having both an adsorption ability specific to an Fc-containing target molecule such as an antibody and an excellent ability of removing impurities such as aggregates, to complete the present invention.

Specifically, the mixed mode antibody affinity separation matrix of the present invention is a mixed mode antibody affinity separation matrix comprising an antibody affinity ligand and a cation exchange group on a single separation matrix.

The dynamic binding capacity of the cation exchange group under the condition of elution pH for a target molecule is preferably not more than two times of the dynamic binding capacity of the antibody affinity ligand under the condition of neutral pH.

Further, it is preferable that the cation exchange group is attached to a separation matrix comprising an antibody affinity ligand.

It is preferable that the antibody affinity ligand is attached to a separation matrix comprising a cation exchange group.

It is preferable that the antibody affinity ligand is at least one selected from protein A, protein G, protein L, protein H, protein D, protein Arp, protein FcγR, a synthetic ligand for binding an antibody and an analog thereof.

It is preferable that the antibody affinity ligand is at least one selected from protein A, protein G, protein L and an analog thereof.

In addition, it is preferable that the antibody affinity ligand is at least one selected from protein A and an analog thereof.

It is preferable that the cation exchange group is a ligand comprising at least one selected from a carboxyl group and a sulfate group.

It is preferable that a base material of a water-insoluble carrier of the separation matrix is made from at least one selected from carbohydrate and derivatives thereof, synthetic polymers and glass.

It is preferable that the structure of the base material of the separation matrix is a porous bead, monolith or membrane.

Further, the present invention is a method for purifying a target molecule using the mixed mode antibody affinity separation matrix.

The elution pH of the target molecule is preferably 6 or less, and the elution pH of the target molecule is preferably 2 or more.

The target molecule is preferably immunoglobulin G, immunoglobulin G derivative, or Fc-containing molecule.

In addition, the present invention is a target molecule purified with the method of the present invention.

Effects of the Invention

According to the present invention, in the first affinity chromatography step of a process for purifying an Fc-containing target molecule such as an antibody, the antibody as the main target substance of the affinity purification can be purified at high purity, the selective separation properties of monomers can also be improved; and the burden on a subsequent impurity removal step can be reduced.

MODE FOR CARRYING OUT THE INVENTION

The mixed mode antibody affinity separation matrix of the present invention is characterized in that both an antibody affinity ligand and a cation exchange group are immobilized to a separation matrix (herein also referred to as a water-insoluble carrier or a carrier) via a covalent bond.

Since the present invention is a mixed mode antibody affinity separation matrix comprising an antibody affinity ligand and a cation exchange group on a water-insoluble carrier, the mixed mode antibody affinity separation matrix of the present invention can be prepared using a separation matrix on which one of the antibody affinity ligand and the cation exchange group is previously immobilized. That is to say, a cation exchange group can be introduced to a separation matrix containing an antibody affinity ligand, or an antibody affinity ligand can be immobilized to a separation matrix containing a cation exchange group. Alternatively, both the antibody affinity ligand and the cation exchange group can be simultaneously immobilized to a water-insoluble carrier.

The antibody affinity ligand, the cation exchange group, the water-insoluble carrier, binding (immobilization) of the antibody affinity ligand and the cation exchange group to the carrier, and the like in the present invention will be explained in detail below.

The "antibody affinity ligand" in the present invention indicates a substance which selectively collects (binds) a target (objective) molecule from a certain group of molecules on the basis of affinity between specific molecules represented by a bond of an antigen and an antibody.

The antibody affinity ligand which can be used in the present invention is not specifically limited, so long as the substance has a characteristic capable of specifically binding to an antibody or an Fc-containing molecule of a constant region of an antibody, as a target molecule. The antibody affinity ligand is preferably a peptide ligand, a protein ligand, or a chemosynthetic ligand (synthesized compound). From the viewpoint of specificity to a target molecule, a peptide ligand or a protein ligand is further preferable. Among them, it is especially preferable that the antibody affinity ligand is protein A, protein G, protein L, protein H, protein D, protein Arp, protein FcγR, a synthetic peptide ligand for binding an antibody and an analog substance thereof. The antibody affinity ligand is more preferably protein A, protein G, protein L and an analog substance thereof, and the antibody affinity ligand is most preferably protein A and an analog substance thereof. The antibody affinity ligand is not specifically limited, so long as the substance has a target molecule-binding domain (a monomer peptide or protein, a single domain). It is preferable that the antibody affinity ligand is a polymer peptide or a protein linked with preferably two or more domains (multiple domains), more preferably 2 to 10 domains, 2 to 8 domains, and further preferably 2 to 6 domains. It is especially preferable that the antibody affinity ligand is a polymer protein linked with 3 to 6 domains. The polymer protein may be a homopolymer such as a homodimer and a homotrimer which is a linked body of a single target molecule-binding domain. The polymer protein may be a heteropolymer such as a heterodimer and a heterotrimer which is a linked body of plural kinds of target molecule-binding domains so long as the target molecules are identical.

As a method for linking the target molecule-binding domains of the antibody affinity ligand of the present invention, a method of not destabilizing a three-dimensional structure of the polymer protein is preferable. The method includes, but not limited to, for example, a method of linking the target molecule-binding domains via a terminal amino acid of the domain sequence, a method of linking the target molecule-binding domains not via an amino acid residue of the domain sequence, or a method of linking the target molecule-binding domains via amino acid residues other than one or plural domain sequences.

As the antibody affinity ligand of the present invention, a fusion protein in which a polymer protein as one component is fused to another protein having a different function can be preferably used. Examples of the fusion protein may include, but not limited to, a protein to which albumin or GST (glutathione S-transferase) are fused, and a protein to which a nucleic acid such as a DNA aptamer, a drug such as an antibiotic, and a macromolecule such as PEG (polyethylene glycol) are fused.

In the present invention, the "cation exchange group" can function as a cation exchange group to capture a target molecule under conditions that an antibody or a Fc-containing molecule of a target molecule is eluted (released) from an antibody affinity ligand. Also, the "cation exchange group" can function as a cation exchange group to elute a monomer and an aggregate of the target molecule in this order in the manner dependent on ionic strength by a counter ion such as sodium ion or potassium ion. For example, the cation exchange group includes a carboxyl group and a sulfate group. It is preferable to prevent the formation of locally acidic environments in the range of the elution pH of the target molecule from the antibody affinity ligand. It is preferable that the cation exchange group is a mildly acidic group. For example, in the case where protein A is used in the antibody affinity ligand, it is preferable that the cation exchange group is a carboxyl group.

A "water-insoluble carrier" used in the present invention is a carrier made of water-insoluble base material, and is not particularly limited so long as the antibody affinity ligand and the cation exchange group are immobilized on the carrier. The water-insoluble carrier includes inorganic carriers such as glass beads and silica gel; organic carriers such as synthetic polymers including cross-linked polyvinyl alcohol, cross-linked polyacrylate, cross-linked polyacrylamide, cross-linked polystyrene and polysaccharides including crystalline cellulose, cross-linked cellulose, cross-linked agarose, cross-linked dextran; and composite carriers of combinations of these carriers such as organic-organic composite carrier and organic-inorganic composite carrier. Examples of commercial products thereof can include GCL 2000 (porous cellulose gel), Sephacryl S-1000 (covalently cross-linked copolymer of allyl dextran and methylene bis acrylamide), Toyopearl (acrylate carrier), Sepharose CL4B or Rapid Run Agarose Beads (cross-linked agarose carrier), Cellufine (cross-linked cellulose carrier) and the like. The water-insoluble carrier can be classified into carbohydrate and derivatives thereof, synthetic polymers, glass and the like. These carriers can be appropriately combined.

In addition, the water-insoluble carrier used in the present invention has desirably a large surface area and is preferably a porous matrix having a large number of fine pores with a suitable size for target antibody molecules and the like, from the viewpoint of productivity to be treated per unit time. The carrier may be any form such as bead, monolith, fiber, or membrane (including hollow fiber), and the carrier can be selected from any form of these. The water-insoluble carrier is preferably a porous bead, monolith, or membrane. The water-insoluble carrier is especially preferably a porous bead because the separation matrix can effectively function by concertedly working the antibody affinity ligand and the cation exchange group arranged on the water-insoluble carrier, causing proximity of physical distance between the antibody affinity ligand and the cation exchange group, and obtaining a given retention time. When the cation exchange group is immobilized on the carrier to which the antibody affinity ligand is fixed, a carrier made of polysaccharides or modified with monosaccharides or polysaccharides is preferable from the viewpoint of easy of introduction of the antibody affinity ligand. Concretely, the carrier is not particularly limited, and is preferably an agarose carrier and a cellulose carrier.

As a method for immobilizing the antibody affinity ligand to the separation matrix, a general method can be used. For example, an amino group of the antibody affinity ligand may bind to a carrier via a formyl group introduced on the carrier, and an amino group of the antibody affinity ligand may bind to a carrier via an activated carboxyl group on the carrier. In addition, these water-insoluble carriers are activated so that the ligand can covalently bind to the carrier before introduction of the antibody affinity ligand. A commercially available activated carrier may be used, and activation may be carried out by an operator himself/herself.

A functional group introduced to the water-insoluble carrier by activation is not specifically limited, so long as the functional group can form a covalent bond with the antibody affinity ligand. Examples of the functional group may include a reactive functional group ("activating group") such as an epoxy group (epichlorohydrin), a hydroxy group activated by cyanogen bromide, N,N-disuccinimidyl carbonate (DSC) and the like, an aldehyde group or an activated carboxylic acid group (for example, N-hydroxysuccinimide (NHS) ester, carbonyldiimidazole (CDI) activated ester), and the like (Hermanson G. T. et al, "Immobilized Affinity Ligand Techniques, Academic Press", 1992, U.S. Pat. Nos. 5,874,165, 3,932,557, 4,772,653, 4,210,723, 5,250,613, EP 13 52957, WO 2004/074471). These functional groups include a functional group in which the antibody affinity ligand directly, covalently binds to the carrier, and a functional group in which a linear, branched, or cyclic linker or spacer is used. Moreover, when the carrier to which the antibody affinity ligand is introduced is activated, it is preferably activated by the technique in which the activated group directly does not react to the ligand.

As a method for immobilizing a protein ligand among the antibody affinity ligands to the carrier, a method for reacting a part of the functional group of the protein with a part of the functional group of the carrier can be used. Examples of the major functional group in the protein which can be utilized for the reaction (activating group) may include, but not limited to, N-terminal amino acid and an amino group of a lysine (Lys) side chain, or a thiol group of a cysteine (Cys) side chain, or C-terminal amino acid and carboxyl groups of a glutamic acid (Glu) side chain and an aspartic acid (Asp) side chain.

In addition, as a method for immobilizing the proteinous antibody affinity ligand to the water-insoluble carrier by controlling the orientation of the ligand, a method of utilizing protein A having cysteine at the C-terminus is proposed (U.S. Pat. No. 6,399,750, Ljungquist C. et al., "Eur. J. Biochem." 1989, Vol. 186, p. 557-561).

Examples of immobilization techniques utilizing a linker may include not only a method of ensuring the distance between the carrier and the ligand to exclude the steric hindrance aiming at provision of high performance, but also a method of giving and forming a functional group (for example, a charged amine) in a linker or a spacer. Improvement of separation performance by improvement of immobilization yield by effectively accumulating the ligand in the portion of a linker or a spacer at the time of immobilization of the antibody affinity ligand has been examined. For example, the immobilization technique includes an immobilization technique of a protein ligand to an agarose carrier derivatized by an NHS-activated carboxylic acid as a part of a linker arm (U.S. Pat. No. 5,260,373, JP2010-133733, JP2010-133734).

In addition, a method for separately immobilizing an antibody affinity ligand on a water-insoluble carrier by utilizing an associative group on the carrier besides a linker or a spacer in which the antibody affinity ligand is accumulated on a carrier without forming a covalent bond between the associative group and the antibody affinity ligand is also proposed (JP2011-256176).

As a technique to immobilize or introduce a cation exchange group to a water-insoluble carrier, when the cation exchange group is introduced before immobilization of the antibody affinity ligand, a technique used for production of a cation exchanger can be usually utilized. For example, a technique to introduce a carboxymethyl group to a sugar skeleton includes, but not limited to, a method of making monochloroacetic acid react under alkaline conditions, and a method of introducing a sulfate group includes, but not limited to, a method of making sulfuric acid react under alkaline conditions. It is also possible to introduce a carboxyl group by introducing an active group which reacts with an amino group on a water-insoluble carrier, and immobilizing an amino acid via an amino group of the amino acid.

When the cation exchange group is introduced after introduction of the antibody affinity ligand, it is preferable to select a technique of minimizing decrease of activity of the antibody affinity ligand. For example, a cation exchange group can be introduced from covalent binding due to reductive amination of the aldehyde group and the amino group on the carrier, by activating the carrier from reaction of sodium periodate with a diol group present in or introduced to the water-insoluble carrier to introduce an aldehyde group, and adding a molecule having an amino group and a cation exchange group in a single molecule, and carrying out reduction treatment after formation of an imine. A method for introducing a carboxyl group of an amino acid is preferable as a method of preparing a material of a separation matrix for antibody purification, from the viewpoint of toxicity in a case where the ligand is leached.

The antibody affinity ligand and the cation exchange group can also be continuously or simultaneously introduced to the water-insoluble carrier. For example, the carrier is activated by reacting sodium periodate to a diol group present in or introduced to the water-insoluble carrier to introduce an aldehyde group. When adding and immobilizing the antibody affinity ligand thereto, a molecule such as an amino acid having an amino group and a cation exchange group in a single molecule is continuously or simultaneously added together. Thus, the antibody affinity ligand and the cation exchange group can be individually introduced to individual aldehyde groups on the water-insoluble carrier by reductive amination.

The cation exchange group may be directly immobilized to the water-insoluble carrier, and may be indirectly immobilized via a spacer, linker and the like. In addition, so long as the cation exchange group can function as a cation exchanger under acidic pH conditions that a target molecule is eluted (released) from the antibody affinity ligand, the cation exchange group, the spacer or the linker may include a functional group having other functions, and the molecular shape thereof is also not particularly limited.

The present invention is a mixed mode antibody affinity separation matrix in which both an antibody affinity ligand and a cation exchange group are immobilized on a carrier composed of a water-insoluble base material via a covalent bond. The mixed mode antibody affinity separation matrix is characterized in that the separation matrix has excellent resolution (for example, selectivity of a monomeric substance, removal performance of an aggregate) due to concerted actions of each separation function by combining different separation functions.

As representative examples of the first chromatography and the second chromatography utilized in the purification platform process of an antibody preparation, for example, a combination of protein A chromatography and cation chromatography is used.

In the first chromatography, the ability of separating a monomeric substance and an aggregate by protein A chromatography used is low, and robustness of the separation is also poor. Thus, in general, elution conditions that high recovery rate can be obtained by minimizing degeneration and aggregation of an antibody or an Fc-containing molecule as a target molecule are selected, and removal of the impurity such as the aggregate and the like is carried out in the subsequent processes.

As the second chromatography, when cation exchange chromatography is selected, the aggregate and other contaminants are generally removed by adsorption and desorption mode. However, in this chromatography, the eluate from the protein A carrier is required to adjust to pH and ionic strength appropriate for adsorption of cation exchange chromatography. Additionally, the ability for separating impurity such as the aggregate and the like depends on a load amount. When separation is prioritized, the load amount is restricted. Thus, while there are a wide variety of controlling factors, efficient separation of the impurity such as the aggregate is not necessarily possible.

On the other hand, when the mixed mode antibody affinity separation matrix of the present invention is used, an excellent separation characteristic is exhibited by concerted functions possessed by both the antibody affinity ligand and the cation exchange group to separate the monomer and the impurity such as the aggregate. Additionally, two steps of the chromatography operations can be shortened to one step, and reduction of the kinds and the amount of the buffer to be used, and shortening of working hours can be expected.

In addition, the mixed mode antibody affinity separation matrix of the present invention can give an elution fraction having high content of monomeric substances by setting of a narrow pH range (preferably pH 3 to 4, more preferably pH 3.1 to 3.9, further preferably pH 3.2 to 3.8) at which the target molecule is eluted from the antibody affinity ligand and an ionic strength (preferably 10 to 500 mM, more preferably 15 to 400 mM, further preferably 20 to 350 mM, "stepwise elution" wherein two or more kinds of salt concentrations which increase gradually in the range are used, or "gradient elution" wherein a salt concentration which gradiently increases in the range is used). Especially in purification of a monoclonal antibody, since the elution pH is significantly separated from the isoelectric point of the target molecule, there is no significant difference in the range of the elution ionic strength of each antibody. Thus, it is possible to set conditions of various target molecules in a narrow range. Furthermore, when modified protein A ligand is used as the antibody affinity ligand, the elution pH range can be set to be further narrower range, and effective washing is also possible due to use of alkaline CIP (cleaning in place; stationary washing). Thus, utilization of modified protein A is preferable from the viewpoint of construction of a robust process.

A separation matrix using a synthesized compound containing an ion exchange group and a hydrophobic group as a ligand, which is generally used as a mixed mode separation matrix, not only has different setting of conditions for each target molecule depending on difference in hydrophobicity and isoelectric point, and the like, but also has low specificity, even if the target molecule is a monoclonal antibody. Thus, it is difficult to make a platform as a recovery step.

On the other hand, the mixed mode antibody affinity separation matrix of the present invention can not only exhibit high specificity with the antibody affinity ligand at the time of adsorption, but also easily set conditions thereof by setting ionic strength in the range of the elution conditions of the antibody affinity ligand. Thus, the mixed mode antibody affinity separation matrix of the present invention is more excellent than an existing mixed mode separation matrix.

More concretely, in the mixed mode antibody affinity separation matrix of the present invention, when a target molecule such as an antibody is adsorbed around neutral pH, it is preferable to add a counter ion of the cation exchange group at a certain concentration or higher. Thus, the cation exchange group does not work under the conditions. In addition, if the cation exchange group works, a nonspecific adsorbate derived from the cation exchange group can be washed and removed with a solution having further higher ionic strength. On the other hand, the ionic strength does not inhibit adsorption of the antibody affinity ligand, and enables adsorption of an objective substance with high specificity. Additionally, a molecule which nonspecifically adsorbs to the base material, the linker, the spacer, the ligand and the target molecule can be effectively washed and removed by use of a washing fluid having high ionic strength.

In general, the mixed mode antibody affinity separation matrix can show high specificity for a recombinant monoclonal antibody which is expressed in a culture supernatant because it contains an ionic strength close to that of a body fluid of a human and the like, even if directly subjected to the separation matrix of the present invention. Additionally, a contaminant can be further reduced by a washing fluid having a higher ionic strength.

Moreover, a method for improving immobilization rate of ligands by noncovalently and effectively accumulating an antibody affinity ligand on a carrier of a base matrix using an ion exchange group or a hydrophobic functional group at the time of immobilization of the ligand to a separation matrix is known (JP2011-256176). This method is essentially different from the present invention in that (1) the ability of separating impurity such as an aggregate and the like is not improved; clearly distinguished from the present invention in principle of preparation in that (2) a cation exchange group of the other ligand of the present invention is not utilized in accumulation of the antibody affinity ligand on the carrier of the base matrix; and clearly distinguished also in terms of the function in that (3) the separation matrix of the present invention has excellent separation characteristics for impurity such as an aggregate.

The mixed mode antibody affinity separation matrix of the present invention can also be prepared by additionally introducing a cation exchange group on an antibody affinity carrier to which the antibody affinity ligand is immobilized. The mixed mode antibody affinity separation matrix of the present invention is characterized in that a desired ion exchange group can be introduced independently of immobilization of the antibody affinity ligand.

In addition, a method of introducing an antibody affinity ligand to an NHS-activated carrier is generally known. However, since, after introducing a protein ligand into a carboxyl group activated by NHS, the carboxyl group is usually inactivated by reaction of the carboxyl group with an amine and the like, there is no case example to utilize the function of the carboxyl group on purpose. Therefore, this general method is clearly distinguished from the present invention introducing a cation exchange group on purpose. In the present invention, a cation exchange group may be introduced either before or after introduction of the antibody affinity ligand, and the method of introducing the ligand is also not limited to the carboxyl group activated by NHS and the like.

A technique to efficiently introduce a carboxyl group to a water-insoluble carrier and a technique to prepare an antibody affinity separation matrix using a carrier of which introduced carboxyl group is activated are disclosed (JP2010-133733, JP2010-133734). However, the technique subsequent to NHS activation is the same as a known method for immobilizing an affinity ligand using any known NHS-activated carrier. The present invention provides a novel mixed mode antibody affinity separation matrix which simultaneously utilizes an antibody affinity ligand and a cation exchange group and which reduces a contaminant such as an aggregate, and a method for using the same. Thus, the present matrix is clearly distinguished from the antibody affinity separation matrix prepared using a conventional NHS-activated carrier.

The mixed mode antibody affinity separation matrix prepared by the present invention can adjust the function thereof by the ratio of the antibody affinity ligand and the cation exchange group. When the binding capacity of the antibody affinity ligand is higher than the binding capacity of the cation exchange group, an antibody tends to be eluted from the carrier at the time of acidic elution even at a low ionic strength. When the binding capacity of the antibody affinity ligand is at the same level as or lower than the binding capacity of the cation exchange group, an antibody eluted from the antibody affinity ligand is strongly retained by the cation exchange group at a low ionic strength, and the antibody tends to be hardly eluted. Thus, in order to obtain a higher recovery rate, it is necessary to set the elution ionic strength to be high. In either case, the recovery rate and the monomer ratio thereof can be controlled by adjusting the ionic strength.

The ratio of the antibody binding capacity of the antibody affinity ligand and the antibody binding capacity of the cation exchange group is not particularly limited. In the mixed mode antibody affinity separation matrix of the present invention, the dynamic binding capacity of a cation exchange group under the condition of elution pH for the target molecule (especially antibody, more preferably human IgG or IgG of humanized monoclonal antibody and the like) is preferably not more than two times, more preferably not more than one time, and especially preferably not more than one fifth with respect to the dynamic binding capacity of an antibody affinity ligand under the condition of antibody adsorption (under the condition of neutral pH) for a target molecule (especially antibody, more preferably human IgG or IgG of humanized monoclonal antibody and the like). The lower limit thereof may be, for example, not less than one hundredth, or not less than one fiftieth. When the amount of antibody binding with the cation exchange group is small, it is possible to set the elution ionic strength low, and there is a tendency that a treatment such as desalting becomes unnecessary in the subsequent antibody purification process. Additionally, the range of setting of the elution ionic strength becomes narrow, so that it is easy to develop the process.

The target molecule to be purified with the mixed mode antibody affinity separation matrix of the present invention is immunoglobulin G and an analog thereof (including a derivative). The target molecule also includes not only a molecule generally called an antibody, but also an Fc fusion protein (Fc-containing molecule) in which an Fc region of a constant region of an immunoglobulin molecule, and another functional protein or peptide are fused. These target molecules are utilized as a raw material of an antibody drug.

Detailed description of the purification method using the mixed mode antibody affinity separation matrix of the present invention will be exemplified herein below by the case where the target molecule is immunoglobulin G, but the present invention is not limited thereto.

Purification of a target molecule (antibody) using the mixed mode antibody affinity separation matrix is roughly composed of 4 steps: an adsorption step, a washing step, a step of adjusting the ionic strength, and an elution step. In addition, purification may comprise a step for reuse such as subsequent regeneration step and/or CIP step, and re-equilibration step.

In the adsorption step, a general purification method of affinity column chromatography can be used. That is to say, in one example thereof, pH of a protein solution comprising immunoglobulin G is adjusted to be near neutral, and thereafter the solution is loaded on a column packed with the mixed mode antibody affinity separation matrix of the present invention, to let the separation matrix specifically adsorb the immunoglobulin G via the antibody affinity ligand. For example, when protein A is the antibody affinity ligand, pH of the protein solution comprising immunoglobulin G is preferably 6 or more, more preferably 6.3 or more and 9 or less, and further preferably 6.5 or more and 8.5 or less. In purification of immunoglobulin G produced by a mammalian cultured cell, not only adjustment of the ionic strength is not especially necessary, but also nonspecific adsorption can also be suppressed by previously increasing the ionic strength.

In the washing step, an appropriate amount of a buffer solution within the range of the conditions under which the antibody affinity ligand functions is let to pass through the column, to wash the column. That is to say, the preferable range of pH may be the same range as that of the above-mentioned case of the adsorption step (near neutral pH). For example, pH is preferably 6 or more. At this point, immunoglobulin G of the target molecule is adsorbed to the mixed mode antibody affinity separation matrix of the present invention. At this time, impurities can be effectively removed in some cases, by optimization of the ionic strength and the composition at near neutral pH. At the time of the loading and washing, conditions under which the cation exchange group does not function is preferable. That is to say, it is preferable that pH is near neutral and that a washing fluid having a certain level or more of ionic strength is utilized, and impurities nonspecifically remaining in the separation matrix and/or in the column via immunoglobulin G can be washed in this process. For example, the ionic strength is preferably 0.2 M or more, and more preferably 0.5 M or more.

In the step of adjusting the ionic strength, a buffer having low ionic strength near neutrality is passed through the column, to prepare an ionic strength-dependent elution function by the cation exchange group.

In the elution step, the target molecule can be separated from a cation exchange group at the time of elution from the antibody affinity ligand by a combination of acidic pH and the ionic strength, to recover a fraction having high monomer content in a fraction eluted at a low ionic strength by concerted actions from the antibody affinity ligand and the cation exchange group. For the pH of the eluate, the elution pH for immunoglobulin G from the antibody affinity ligand can be applied. Since the pH is determined on the basis of the separation conditions by the kind of the mixed mode antibody affinity separation matrix consisting of the antibody affinity ligand used for production of the matrix and of immunoglobulin G, it is unnecessary to set special conditions.

In the case where protein A is used as the antibody affinity ligand, it is preferable that the elution pH is 2 or more and 6 or less. In order to prevent acidic denature of a target molecule, the elution pH is preferably 3.0 or more, more preferably 3.3 or more, and especially preferably 3.5 or more. The elution pH is preferably 5.5 or less, and more preferably 5.0 or less.

When an alkali-resistant type of a protein A ligand is used, the elution pH thereof is generally mainly set within the range of 3.5 to 4.0, but not limited thereto. In addition, the ionic strength for the elution not only depends on the introduction ratio of the antibody affinity ligand and the cation exchange group, but also depends on the load amount of immunoglobulin G per unit volume. However, the optimized conditions can be easily set by a gradient elution experiment or a stepwise elution experiment.

In the elution of antibodies from the mixed mode antibody affinity separation matrix prepared by the present invention, either gradient elution or stepwise elution with salt concentration is applicable. From the viewpoint of reduction of the amount of the eluate, stepwise elution with the ionic strength is preferable. Furthermore, from the viewpoint of simplification of the operation, it is preferable to set conditions for one-step elution such that recovery of an antibody and high content of a monomer can be accomplished.

Moreover, when impurity including an aggregate remains in the column and is not mixed in the elution fraction even with the combination of the ionic strength of the washing step and acidic pH, the step of adjusting the ionic strength can be omitted.

When the immunoglobulin G is purified by the mixed mode antibody affinity separation matrix of the present invention, higher monomer selectivity is exhibited than that of an antibody affinity separation matrix based on a single separation mode, and the monomer content in the eluate thereof is high.

When an antibody affinity separation matrix is used in a single separation mode, the monomer content can also be increased to some extent by optimization of the elution pH and the ionic strength, and the like. However, the effect of increase of the monomer content is small, and exertion of the effect is accompanied by significant reduction of the recovery rate. By using the mixed mode antibody affinity separation matrix of the present invention, affinity purification with high specificity and improvement of the monomer content which can be accomplished mainly by cation exchange chromatography can be efficiently accomplished by a single chromatography operation with retaining the high recovery rate. Therefore, it is possible to reduce the burden on the subsequent process, and to contribute to improvement of yield of the whole process and improvement of the monomer content. Thus, use of the novel mixed mode antibody affinity separation matrix of the present invention enables to contribute to improvement of productivity in the process of producing an antibody preparation and to high purification thereof.

The present application claims the benefit of priority to Japanese Patent Application Number 2012-193069 filed on Sep. 3, 2012. The entire contents of the specification of Japanese Patent Application Number 2012-193069 filed on Sep. 3, 2012 are hereby incorporated by reference.

EXAMPLES

The present invention will be explained more in detail on the basis of the Examples herein below, but the present invention is not limited to these Examples.

Preparation Example 1 of Carrier

Preparation of Protein A-Immobilized Carrier

As 4% agarose beads, 4 mL in wet volume of LOW Density GLYOXAL 4 Rapid Run (Agarose Bead Technologies) substituted with water were taken into a reaction vessel, and made up for the slurry volume of 5 mL with water. Thereafter, 1 mL of a 0.25 M sodium citrate solution (pH 3.5) was added thereto. Furthermore, 2 mL of 0.8 M sodium periodate was added thereto, and the mixture was overturned and stirred at room temperature for 0.5 hours, to give a carrier to which an aldehyde group was introduced. Slurry of this carrier was sufficiently washed with water and Dulbecco's PBS (−) (NISSUI PHARMACEUTICAL CO., LTD) (hereinafter PBS) as a phosphate buffer. After recovery, the amount of the slurry was made up for 5 mL. Next, 5 mL of a mixed solution (pH 6.8) of 0.1 M sodium phosphate, 1 M sodium citrate and 0.3 M sodium chloride was added thereto. After mixing the mixture, the amount of the solution was adjusted to 5.5 mL. An aqueous 5 N sodium hydroxide solution was added thereto, to adjust the pH of the slurry including the carrier to 11.5 to 12. Thereafter, 100 mg of protein A was immediately added thereto, and the mixture was stirred under conditions of 2 to 8° C. for 2.5 hours. The pH of the carrier slurry was adjusted to 7 to 5 using a 1 M citric acid solution, and thereafter 0.5 mL of 1M dimethylamine borane was added thereto. The mixture was overturned and stirred at room temperature overnight. The mixture was sufficiently washed with water, 0.1 M citric acid, 0.1 M sodium hydroxide and PBS, to give a protein A carrier in which protein A was covalently immobilized (bound) to agarose (hereinafter referred to as carrier 1). Here, the protein A herein used was prepared on the basis of Examples of WO 2011/118699.

Regarding the carrier 1, antibody binding capacity, especially dynamic binding capacity of the antibody affinity separation matrix was determined. Concretely, as 10% dynamic binding capacity (Dynamic binding capacity; DBC), the amount of IgG adsorption per 1 mL of carrier was calculated from the value obtained by dividing the amount of antibody bound to the column by the time of leakage of 10% of the loaded IgG other than the fraction such as IgG3 which does not bind to the protein A carrier by the volume of the carrier in the column. The chromatography conditions are shown below, and the dynamic binding capacity at 6 minutes of contact time was found by setting the flow rate at the time of loading as 0.4 mL/min. Moreover, the flow rate besides loading was set as 0.6 mL/min (contact time: 4 minutes).

Regarding the carrier 1, 10% DBC of the antibody affinity separation matrix at 6 minutes of contact time was 56.0 mg. Chromatography Condition Used for Determination of 10% DBC Based on Antibody Affinity Ligand
column: ID 0.66 cm×Height 7 cm (manufactured by Omnifit Ltd.)
flow rate: 0.4 mL/min (contact time: 6 minutes) or 0.6 mL/min (contact time: 4 minutes)
polyclonal antibody (IgG): gamma globulin NICHIYAKU (human immunoglobulin G) (NIHON PHARMACEUTICAL CO., LTD.)
loading solution: 2.5 mg-IgG/mL (PBS: Dulbecco Nissui)
equilibrating solution: PBS (pH 7.4)
eluate: 50 mM acetic acid, 0.1 M sodium chloride (pH 3.75)
regeneration solution: 0.1 M acetic acid, 1 M sodium chloride
CIP solution: 0.1 M sodium hydroxide, 1 M sodium chloride
neutralizing and re-equilibrating solution: PBS (pH 7.4)

Preparation Example 2 of Carrier

Preparation of Mixed Mode Antibody Affinity Separation Matrix by Immobilization of Protein A to Carboxyl Group-Introduced Carrier As 4% agarose beads, 4 mL in wet volume of LOW Density GLYOXAL 4 Rapid Run (Agarose Bead Technologies) substituted with water were taken into a reaction vessel, and made up for the slurry volume of 5 mL with water. Thereafter, 1 mL of a 0.25 M sodium citrate solution (pH 3.5) was added thereto. Next, 1 mL of a mixed solution (pH 3.5) of 0.1 M citric acid and 0.1 M glutamic acid was added thereto, and the mixture was stirred. Furthermore, 0.5 mL of 0.8 M sodium periodate was added thereto, and the mixture was overturned and stirred at room temperature for 1 hour, to introduce an aldehyde group on the carrier of agarose beads. Slurry of this carrier was washed 5 times with 1 M glutamic acid/PBS (pH 7) diluted to 100 times with cold water. After recovery, the amount of the slurry was made up for 5 mL. To the slurry, 5 mL of 1 M glutamic acid/PBS (pH 7) was added, and the mixture was overturned and stirred at room temperature for 2 hours. Thereafter, 0.5 mL of an aqueous 1 M dimethylamine borane solution was additionally put thereto, and the mixture was overturned and stirred at room temperature overnight. The carrier was precipitated by centrifugation, and thereafter the supernatant was removed so that the liquid amount became 6 mL. Twenty milligrams of sodium borohydride was directly added thereto, and the mixture was further overturned and stirred at room temperature for 2 hours. The mixture was sufficiently washed with water, 0.1 M citric acid, 0.1 M sodium hydroxide and PBS containing 0.5 M NaCl was added, to give an agarose carrier in which a carboxyl group was introduced to an aldehyde group by reductive amination via an amino group of glutamic acid.

Next, the agarose carrier to which a carboxyl group was introduced was washed with 0.1 M MES and 0.5 M NaCl (pH 6) (MES buffer) and the solution was substituted. Thereafter, 4 mL in wet volume of the carrier was taken into a reaction vessel, and the slurry volume was made up for 5 mL. To the slurry, 5 mL of an NHS/EDC solution prepared by dissolving 0.25 g of NHS per 20 mL of MES buffer and subsequently dissolving 1.5 g of EDC was added, and the mixture was overturned and stirred at room temperature for 15 minutes. Thereafter, the mixture was sufficiently washed with cooled PBS, to give an agarose carrier in which a part of carboxyl group is modified with EDC/NHS. The amount of the solution was adjusted to 7 mL, and 80 mg of protein A was added thereto. The mixture was overturned and stirred for 2 hours. The mixture was substituted and washed with a 0.1 N sodium hydroxide solution, and the carboxyl group which was modified with EDC/NHS and did not react with protein A was regenerated, to give the mixed mode antibody affinity separation matrix of the present invention as a protein A carrier to which a carboxyl group was introduced (hereinafter referred to as carrier 2). Here, the protein A used herein was prepared on the basis of Examples of WO 2011/118699.

Regarding the carrier 2, the antibody binding capacity of the antibody affinity ligand was determined. The determination method was the same as that of Preparation Example 1 of carrier. As a result, 10% DBC at 6 minutes of contact time was 10.2 mg.

Next, regarding the carrier 2, the antibody binding capacity of the cation exchange group was determined. As conditions for loading the antibody, a 10 mM acetate buffer at pH 3.5 was used such that protein A of the antibody affinity ligand hardly had antibody-capturing ability, and the carboxyl group introduced as a cation exchange group could function. Since the cation exchange group did not exhibit selectivity for IgG 3 and the like unlike the protein A ligand, as 10% DBC, the amount of IgG adsorption per 1 mL of carrier was calculated by dividing the amount of antibody bound to the column from the start of the loading to the time of leakage of 10% of the entire loaded IgG by the volume of the carrier in the column. The chromatography conditions are shown below, and the dynamic binding capacity at 6 minutes of contact time was found by setting the flow rate at the time of loading as 0.4 mL/min. Moreover, the flow rate besides loading was set as 0.6 mL/min (contact time: 4 minutes). Regarding the carrier 2, 10% DBC based on introduction of the cation exchange group under antibody elution conditions at 6 minutes of contact time was 10.6 mg.

As described above, the carrier 2 to be used in the mixed mode antibody affinity separation matrix of the present invention could be obtained, so that the antibody binding capacity based on the cation exchange group was slightly higher than the antibody binding capacity based on the antibody affinity ligand.

Chromatography Condition Used for Determination of 10% DBC Based on Cation Exchange Group column: ID 0.66 cm×Height 7 cm (manufactured by Omnifit Ltd.)
flow rate: 0.4 mL/min (contact time: 6 minutes) or 0.6 mL/min (contact time: 4 minutes)
polyclonal antibody (IgG): gamma globulin NICHIYAKU (NIHON PHARMACEUTICAL CO., LTD.)
loading solution: 2.5 mg-IgG/mL (10 mM acetic acid: pH 3.5)
equilibrating solution: 10 mM acetic acid (pH 3.5)
eluate: 10 mM acetic acid, 0.5 M sodium chloride (pH 3.5)
CIP solution: 0.1 M sodium hydroxide, 1 M sodium chloride
neutralizing and re-equilibrating solution: 10 mM acetic acid (pH 3.5)

Preparation Example 3 of Carrier

Preparation of Mixed Mode Antibody Affinity Separation Matrix by Immobilization of Carboxyl Group to Protein A-Introduced Carrier Using MabSelect SuRe (GE Healthcare Biosciences, carrier 3) as a protein A-immobilized carrier, a carboxyl group was introduced to MabSelect SuRe substituted with a 0.5 M saline solution. 4 mL in wet volume of the carrier 3 was taken in a reaction vessel, and the slurry volume was made up for 5 mL. Thereafter, 1 mL of a 0.25 M sodium citrate solution (pH 3.5) was added thereto. Next, 1 mL of a 0.1 M citric acid and 0.1 M glutamic acid solution (pH 3.5) was added thereto, and the mixture was stirred. To the mixture, 0.5 mL of 0.8 M sodium periodate was added, and the mixture was overturned and stirred at room temperature for 1 hour, to introduce an aldehyde group on the carrier 3. This carrier slurry was washed 5 times with 1 M glutamic acid/PBS (pH 7) diluted to hundred times with cold water. After recovery, the liquid amount of the slurry was made up for 5 mL. To the slurry, 5 mL of 1 M glutamic acid/PBS (pH 7) was added, and the mixture was overturned and stirred at room temperature for 2 hours. Thereafter, 0.5 mL of an aqueous 1 M dimethylamine borane solution was additionally added thereto, and the mixture was overturned and stirred at room temperature overnight. The carrier was precipitated by centrifugation, and thereafter the supernatant was removed so that the liquid amount became 6 mL. Twenty milligrams of sodium borohydride was directly added thereto, and the mixture was further overturned and stirred at room temperature for 2 hours. The mixture was sufficiently washed with water, 0.1 M citric acid, 0.1 M sodium hydroxide and PBS containing 0.5 M NaCl, to give the mixed mode antibody affinity separation matrix of the present invention as a protein A carrier in which a carboxyl group was introduced to an aldehyde group by reductive amination via an amino group of glutamic acid (hereinafter referred to as carrier 4).

Regarding the carrier 4, antibody binding capacity based on the antibody affinity ligand was determined. The determination method was the same as that of Preparation Example 1 of carrier. As a result, 10% DBC at 6 minutes of contact time was 42.4 mg.

Next, regarding the carrier 4, the antibody binding capacity based on the cation exchange group was determined. The determination method was the same as that of Example 1. As a result, 10% DBC at 6 minutes of contact time was 4.2 mg.

As described above, the carrier 4 to be used in the mixed mode antibody affinity separation matrix of the present invention could be obtained, so that the antibody binding capacity based on the cation exchange group was about one tenth the antibody binding capacity based on the antibody affinity ligand.

In addition, regarding carrier 3 of the protein A-immobilized carrier used as the material of the carrier 4, the antibody binding capacity as the antibody affinity separation matrix was determined. As a result, 10% DBC at 6 minutes of contact time was 50.3 mg.

Comparative Example 1

Stepwise Salt Elution and Separation of Aggregate Under Acidic Conditions of Protein A-Immobilized Carrier (Carrier 1)

Using the carrier 1 with a column (manufactured by Omnifit Ltd. (ID 0.66 cm×Height 7 cm)) prepared and used for evaluation in Preparation Example 1 of carrier, 7 mg of human polyclonal antibody per 1 mL of carrier was loaded to this column under neutral conditions, to elute the antibody with an elution buffer having various ionic strengths under acidic conditions (chromatography condition 1 for separation of aggregate).

Each eluate was analyzed by gel filtration chromatography, and the protein content and yield (Yield) were found from the protein peak area value of each elution fraction (fraction), and the ratio of a monomeric substance (monomer) and an aggregate (polymer) and the like was further found from the protein peak analysis, to calculate monomeric substance content (Monomer content) and monomeric substance yield (Monomer Yield). At this time, the total sum of the area values of the elution fractions from carrier 1 was regarded as 100%, and each elution fraction was evaluated. Moreover, in order to prevent aggregate formation in the elution fraction from the affinity separation matrix, arginine was added to each eluate so that the final concentration became 0.05 M or more, and the pH of each eluate was adjusted to 5 to 6 using a sodium phosphate solution of pH 5. The mixture was subjected to gel filtration chromatography. Here, each chromatography condition is shown below.

Chromatography Condition 1 for Separation of Aggregate (Acidic pH, Stepwise Salt Elution)
column: ID 0.66 cm×Height 7 cm (manufactured by Omnifit Ltd.)
flow rate: 0.6 mL/min (contact time: 4 minutes)
polyclonal antibody (IgG): gamma globulin NICHIYAKU (NIHON PHARMACEUTICAL CO., LTD.)
loading solution: 2.5 mg-IgG/mL (PBS: Dulbecco Nissui)
equilibrating solution: PBS (pH 7.4) (3CV, CV: column volume)
loading solution: 6.8 mL
washing solution after loading: PBS (pH 7.4) (5CV)
washing solution before elution: 10 mM Tris/HCl (pH7) (5CV)
eluate 1: 10 mM acetic acid (pH 3.5)(8CV)
eluate 2: 10 mM acetic acid containing 150 mM sodium chloride (pH 3.5)(8CV)
eluate 3: 10 mM acetic acid containing 300 mM sodium chloride (pH 3.5)(4CV)
CIP solution: 0.1 M sodium hydroxide, 1 M sodium chloride (4CV) neutralizing and re-equilibrating solution: PBS (pH 7.4)
Gel Filtration Chromatography Condition
column: Superdex 200 10/300 GL (ID 1 cm×Height 30 cm) (manufactured by GE Healthcare Biosciences)
flow rate: 0.5 mL/min
detection wavelength: 214 nm
loading solution: 100 µL/injection (diluted within a range in which the absorbance value does not exceed 1)
eluate: PBS (pH 7.4)

The results of evaluation of stepwise salt elution and separation characteristic for an aggregate under acidic conditions of the carrier 1 are shown in Table 1.

TABLE 1

| elution fraction | carrier 1 | % |
|---|---|---|
| eluate 1(0 mM NaCl) | antibody yield (%) | 99.4 |
| | monomer content (%) | 94.5 |
| | monomer yield (%) | 99.5 |
| eluate 2(150 mM NaCl) | antibody yield (%) | 0.6 |
| | monomer content (%) | 86.3 |
| | monomer yield ( % ) | 0.5 |
| eluate 3(300 mM NaCl) | antibody yield (%) | 0.0 |
| | monomer content (%) | 0.0 |
| | monomer yield (%) | 0.0 |
| eluate 1 + eluate 2 | antibody yield (%) | 100.0 |
| | monomer content (%) | 94.5 |
| | monomer yied (%) | 100.0 |

Example 1

Stepwise Salt Elution and Separation of Aggregate Under Acidic Conditions of Mixed Mode Antibody Affinity Separation Matrix (Carrier 2)

Using the carrier 2 with a column (manufactured by Omnifit Ltd. (ID 0.66 cm×Height 7 cm)) prepared and used for evaluation in Preparation Example 2 of carrier, 7 mg of human polyclonal antibody per 1 mL of carrier was loaded to this column under neutral conditions in the same manner as in Comparative Example 1, to elute the antibody with an elution buffer having various ionic strengths under acidic conditions. Here, the ionic strength of eluate 2 was set as three grades to carry out evaluation (chromatography condition 2 for separation of aggregate).

Each eluate was analyzed by gel filtration chromatography, and the protein content and yield (Yield) were found from the protein peak area value of each elution fraction (fraction), and the ratio of a monomeric substance (monomer) and an aggregate (polymer) and the like was further found from the protein peak analysis, to calculate monomeric substance content (Monomer content) and monomeric substance yield (Monomer Yield). At this time, the total sum of the area values of the elution fractions from carrier 1 evaluated in Comparative Example 1 was regarded as 100%, and each elution fraction was evaluated. Moreover, in order to prevent aggregate formation in the elution fraction from the affinity separation matrix, arginine was added to each eluate so that the final concentration became 0.05 M or more, and the pH of each eluate was adjusted to 5 to 6 using a sodium phosphate solution of pH 5. The mixture was subjected to gel filtration chromatography. Moreover, each chromatography condition is shown below. Additionally, gel filtration chromatography was evaluated in the same manner as in Comparative Example 1.

Chromatography Condition 2 for Separation of Aggregate (Acidic pH, Stepwise Salt Elution)
column: ID 0.66 cm×Height 7 cm (manufactured by Omnifit Ltd.)
flow rate: 0.6 mL/min (contact time: 4 minutes)
polyclonal antibody (IgG): gamma globulin NICHIYAKU (NIHON PHARMACEUTICAL CO., LTD.)
loading solution: 2.5 mg-IgG/mL (PBS: Dulbecco Nissui)
equilibrating solution: PBS (pH 7.4) (3CV)
loading solution: 6.8 mL
washing solution after loading: PBS (pH 7.4) (5CV)
washing solution before elution: 10 mM Tris/HCl (pH7) (5CV)
eluate 1: 10 mM acetic acid (pH 3.5)(8CV)
eluate 2: 10 mM acetic acid containing 150 mM, 175 mM or 200 mM sodium chloride (pH 3.5) (8CV)
eluate 3: 10 mM acetic acid containing 300 mM sodium chloride (pH 3.5) (4CV)
CIP solution: 0.1 M sodium hydroxide, 1 M sodium chloride (4CV) neutralizing and re-equilibrating solution: PBS (pH 7.4)

The results of evaluation of stepwise salt elution and separation characteristic for an aggregate under acidic conditions of the carrier 2 are shown in Table 2.

TABLE 2

| elution fraction | carrier 2 | NaCl concentration of elution 2 | | |
|---|---|---|---|---|
| | | 150 mM | 175 mM | 200 mM |
| eluate 1(0 mM NaCl) | antibody yield (%) | 0.0 | 0.0 | 0.0 |
| | monomer content (%) | 0.0 | 0.0 | 0.0 |
| | monomer yield (%) | 0.0 | 0.0 | 0.0 |
| equate 2(various NaCl concentrations) | antibody yield (%) | 75.1 | 88.3 | 91.6 |
| | monomer content (%) | 99.0 | 98.3 | 97.6 |
| | monomer yield (%) | 78.7 | 91.9 | 94.7 |
| eluate 3(300 mM NaCl) | antibody yield (%) | 18.0 | 6.9 | 1.9 |
| | monomer content (%) | 89.0 | 84.0 | 81.2 |
| | monomer yield (%) | 16.9 | 6.1 | 1.6 |
| eluate 1 + eluate 2 | antibody yield (%) | 75.1 | 88.3 | 91.6 |
| | monomer content (%) | 99.0 | 98.3 | 97.6 |
| | monomer yield (%) | 78.7 | 91.9 | 94.7 |

According to the results in Tables 1 and 2, the carrier 1 indicated that 99% or more of the antibodies were eluted even when the ionic strength of NaCl was 0 at the time of acidic elution [elution fraction in Table 1: eluate 1 (0 mM NaCl)]. On the contrary, the carrier 2 of the mixed mode antibody affinity separation matrix of the present invention exhibited ionic strength-dependent elution behavior by the function of the cation exchange group under the acidic elution conditions [elution fraction in Table 2: eluate 2 (150 mM, 175 mM, 200 mM NaCl)] and significantly improved monomer selectivity as a concerted effect of the protein A ligand and the cation exchange group. Thus, the carrier 2 of the present invention concertedly exhibited each of the characteristics of the protein A ligand and the cation exchange group, and exhibited high specificity and high monomer selectivity in one chromatography step.

Moreover, the carrier 2 had slightly higher antibody binding capacity based on the cation exchange group than that of the protein A affinity ligand under conditions of elution pH of antibody from protein A, and required high ionic strength of a certain concentration or more for elution of the antibody.

Comparative Example 2

Stepwise Salt Elution and Separation of Aggregate Under Acidic Conditions of Protein a Immobilized Carrier (Carrier 3)

Using the carrier 3 with a column (manufactured by Omnifit Ltd. (ID 0.66 cm×Height 7 cm)) used for evaluation in Preparation Example 3 of carrier, 7 mg of human polyclonal antibody per 1 mL of carrier was loaded to this column under neutral conditions, to elute the antibody with an elution buffer having various ionic strengths under acidic conditions (chromatography condition 3 for separation of aggregate).

Each eluate was analyzed by gel filtration chromatography, and the protein content and yield (Yield) were found from the protein peak area value of each elution fraction (fraction), and the ratio of a monomeric substance (monomer) and an aggregate (polymer) and the like was further found from the protein peak analysis, to calculate monomeric substance content (Monomer content) and monomeric substance yield (Monomer Yield). At this time, the total sum of the area values of the elution fractions from the carrier 3 was regarded as 100%, and each elution fraction was evaluated. Moreover, in order to prevent aggregate formation in the elution fraction from the affinity separation matrix, arginine was added to each eluate so that the final concentration became 0.05 M or more, and the pH of each eluate was adjusted to 5 to 6 using a sodium phosphate solution of pH 5. The mixture was subjected to gel filtration chromatography. Moreover, each chromatography condition is shown below. Additionally, gel filtration chromatography was evaluated in the same manner as in Comparative Example 1.

Chromatography Condition 3 for Separation of Aggregate (Acidic pH, Stepwise Salt Elution)
column: ID 0.66 cm×Height 7 cm (manufactured by Omnifit Ltd.)
flow rate: 0.6 mL/min (contact time: 4 minutes)
polyclonal antibody (IgG): gamma globulin NICHIYAKU (NIHON PHARMACEUTICAL CO., LTD.)
loading solution: 2.5 mg-IgG/mL (PBS: Dulbecco Nissui)
equilibrating solution: PBS (pH 7.4) (3CV)
loading solution: 6.8 mL
washing solution after loading: PBS (pH 7.4) (5CV)
washing solution before elution: 10 mM Tris/HCl (pH7) (5CV)
eluate 1: 10 mM acetic acid (pH 3.5)(8CV)
eluate 2: 10 mM acetic acid containing 50 mM sodium chloride (pH 3.5) (8CV)
eluate 3: 10 mM acetic acid containing 300 mM sodium chloride (pH 3.5) (4CV)
CIP solution: 0.1 M sodium hydroxide, 1 M sodium chloride (4CV)
neutralizing and re-equilibrating solution: PBS (pH 7.4)

The results of evaluation of stepwise salt elution and separation characteristic for an aggregate under acidic conditions of the carrier 3 are shown in Table 3. Here, the whole antibodies were eluated up to eluate 2, and data of eluates 1 and 2 are shown in Table 3.

TABLE 3

| elution fraction | carrier 3 | % |
|---|---|---|
| eluate 1(0 mM NaCl) | antibody yield (%) | 99.7 |
| | monomer content (%) | 94.5 |
| | monomer yield (%) | 99.7 |

TABLE 3-continued

| elution fraction | carrier 3 | % |
|---|---|---|
| eluate 2(50 mM NaCl) | antibody yield (%) | 0.3 |
| | monomer content (%) | 100.0 |
| | monomer yield (%) | 0.3 |
| eluate 1 + eluate 2 | antibody yield (%) | 100.0 |
| | monomer content (%) | 94.5 |
| | monomer yield (%) | 100.0 |

Example 2

Stepwise Salt Elution and Separation of Aggregate Under Acidic Conditions of Mixed Mode Antibody Affinity Separation Matrix (Carrier 4)

Using the carrier 4 with a column (manufactured by Omnifit Ltd. (ID 0.66 cm×Height 7 cm)) used for evaluation in Preparation Example 3 of carrier, 7 mg of human polyclonal antibody per 1 mL of carrier was loaded to this column under neutral conditions in the same manner as in Comparative Example 2, to elute the antibody with an elution buffer having various ionic strengths under acidic conditions. The ionic strength of eluate 2 was set as three grades to carry out evaluations (chromatography condition 4 for separation of aggregate).

Each eluate was analyzed by gel filtration chromatography, and the protein content and yield (Yield) were found from the protein peak area value of each elution fraction (fraction), and the ratio of a monomeric substance (monomer) and an aggregate (polymer) and the like was further found from the protein peak analysis, to calculate monomeric substance content (Monomer content) and monomeric substance yield (Monomer Yield). At this time, the total sum of the area values of the elution fractions from carrier 3 evaluated in Comparative Example 2 was regarded as 100%, and each elution fraction was evaluated. Moreover, in order to prevent aggregate formation in the elution fraction from the affinity separation matrix, arginine was added to each eluate so that the final concentration became 0.05 M or more, and the pH of each eluate was adjusted to 5 to 6 using a sodium phosphate solution of pH 5. The mixture was subjected to gel filtration chromatography. Moreover, each chromatography condition is shown below. Additionally, gel filtration chromatography was evaluated in the same manner as in Comparative Example 1.

Chromatography Condition 4 for Separation of Aggregate (Acidic pH, Stepwise Salt Elution)
column: ID 0.66 cm×Height 7 cm (manufactured by Omnifit Ltd.)
flow rate: 0.6 mL/min (contact time: 4 minutes)
polyclonal antibody (IgG): gamma globulin NICHIYAKU (NIHON PHARMACEUTICAL CO., LTD.)
loading solution: 2.5 mg-IgG/mL (PBS: Dulbecco Nissui)
equilibrating solution: PBS (pH 7.4) (3CV)
loading solution: 6.8 mL
washing solution after loading: PBS (pH 7.4) (5CV)
washing solution before elution: 10 mM Tris/HCl (pH7) (5CV)
eluate 1: 10 mM acetic acid (pH 3.5)(8CV)
eluate 2: 10 mM acetic acid containing 25 mM, 50 mM, or 75 mM sodium chloride (pH 3.5)(8CV)
eluate 3: 10 mM acetic acid containing 300 mM sodium chloride (pH 3.5) (4CV)
CIP solution: 0.1 M sodium hydroxide, 1 M sodium chloride (4CV)
neutralizing and re-equilibrating solution: PBS (pH 7.4)

The results of evaluation of stepwise salt elution and separation characteristic for an aggregate under acidic conditions of the carrier 4 are shown in Table 4. Here, in order to compare with Table 3 of Comparative Example 2, results up to eluate 2 are shown in Table 4 in the present Example.

TABLE 4

| | | NaCl concentration of elution 2 | | |
|---|---|---|---|---|
| elution fraction | carrier 4 | 25 mM | 50 mM | 75 mM |
| eluate 1(0 mM NaCl) | antibody yield (%) | 59.7 | 58.9 | 59.1 |
| | monomer content (%) | 98.7 | 98.5 | 98.6 |
| | monomer yield (%) | 62.3 | 61.4 | 61.7 |
| eluate 2(various NaCl concentrations) | antibody yield (%) | 32.1 | 38.7 | 40.8 |
| | monomer content (%) | 97.9 | 94.7 | 92.6 |
| | monomer yield (%) | 33.3 | 38.8 | 40.0 |
| eluate 1 + eluate 2 | antibody yield (%) | 91.8 | 97.6 | 99.9 |
| | monomer content (%) | 98.4 | 97.0 | 96.2 |
| | monomer yield (%) | 95.6 | 100.2 | 101.7 |

According to the results in Tables 3 and 4, the carrier 3 indicated that 99% or more of the antibodies were eluted even when the ionic strength of NaCl was 0 at the time of acidic elution [elution fraction in Table 3: eluate 1 (0 mM NaCl)]. On the contrary, the carrier 4 of the mixed mode antibody affinity separation matrix of the present invention exhibited ionic strength-dependent elution behavior by the function of the cation exchange group under acidic elution conditions [elution fraction in Table 4: eluate 1 (0 mM NaCl) and eluate 2 (25 mM, 50 mM, 75 mM NaCl)] and significantly improved monomer selectivity as a concerted effect of the protein A ligand and the cation exchange group. Thus, the carrier 4 of the present invention concertedly exhibited each of the characteristics of the protein A ligand and the cation exchange group, and exhibited high specificity and high monomer selectivity in one chromatography step.

Moreover, regarding the carrier 4, the antibody binding capacity based on the cation exchange group was about one tenth the antibody binding capacity based on the protein A affinity ligand under antibody elution pH conditions from protein A. When elution pH was 3.5, 80% or more of the antibodies were eluted even when the ionic strength of NaCl was 0. The ionic strength to elute almost entire antibodies was low as compared with Example 1.

Comparative Example 3

Acidic pH Dependent Elution and Separation of Aggregate of Protein A-Immobilized Carrier (Carrier 3)

Using the carrier 3 with a column (manufactured by Omnifit Ltd. (ID 0.66 cm×Height 7 cm)) used for evaluation in Preparation Example 3 of carrier, 7 mg of human polyclonal antibody per 1 mL of carrier was loaded to this column under neutral conditions, to elute the antibody with an elution buffer at various acidic pH under acidic conditions and lower ionic strengths (chromatography condition 5 for separation of aggregate).

Each eluate was analyzed by gel filtration chromatography, and the protein content and yield (Yield) were found from the protein peak area value of each elution fraction (fraction), and the ratio of a monomeric substance (monomer) and an aggregate (polymer) and the like was further found from the protein peak analysis, to calculate monomeric substance content (Monomer content) and monomeric substance yield (Monomer Yield). At this time, the total sum of the area values of each of the elution fractions from each chromatography was regarded as 100%, and difference under conditions of each elution pH was evaluated. Moreover, in order to prevent aggregate formation in the elution fraction from the affinity separation matrix, arginine was added to each eluate so that the final concentration became 0.05 M or more, and the pH of each eluate was adjusted to 5 to 6 using a sodium phosphate solution of pH 5. The mixture was subjected to gel filtration chromatography. Moreover, each chromatography condition is shown below. Additionally, gel filtration chromatography was evaluated in the same manner as in Comparative Example 1.

Chromatography Condition 5 for Separation of Aggregate (Acidic pH Elution)

column: ID 0.66 cm×Height 7 cm (manufactured by Omnifit Ltd.)
flow rate: 0.6 mL/min (contact time: 4 minutes)
polyclonal antibody (IgG): gamma globulin NICHIYAKU (NIHON PHARMACEUTICAL CO., LTD.)
loading solution: 2.5 mg-IgG/mL (PBS: Dulbecco Nissui)
equilibrating solution: PBS (pH 7.4) (3CV)
loading solution: 6.8 mL
washing solution after loading: PBS (pH 7.4) (5CV)
eluate: 10 mM acetic acid (pH 3.25, pH 3.5, or pH 3.75) (8CV)
regeneration solution: 0.1 M acetic acid (4CV)
CIP solution: 0.1 M sodium hydroxide, 1 M sodium chloride (4CV)
neutralizing and re-equilibrating solution: PBS (pH 7.4)

The results of evaluation of acidic pH dependent elution and separation characteristic for an aggregate of the carrier 3 are shown in Table 5.

TABLE 5

| elution fraction | carrier 3 | eluation pH | | |
|---|---|---|---|---|
| | | 3.25 | 3.5 | 3.75 |
| eluate (various pH) | antibody yield (%) | 100.0 | 99.7 | 89.3 |
| | monomer content (%) | 94.5 | 94.5 | 96.1 |
| | monomer yield (%) | 100.0 | 99.7 | 90.2 |

According to the results of Table 5, the monomer content in the eluate could be increased by selecting the elution pH [elution fraction in Table 5: eluate (pH 3.75)] such that a part of adsorbed IgGs remains in the carrier by exertion of moderate monomer selectivity originally possessed by the protein A-immobilized carrier. However, reduction rate of the monomeric substance (monomer) yield was large as compared with that of the carrier 4 of the present invention [elution fraction in Table 4: eluate 1 (0 mM NaCl)+eluate 2 (25 mM NaCl)] shown as the results of Table 4, and the rate of increase in the monomeric substance (monomer) content was small. Thus, the mixed mode antibody affinity separation matrix of the present invention had an excellent characteristic that high monomeric substance (monomer content) can be obtained at high monomeric substance (monomer) yield as compared with that of the antibody affinity separation matrix.

Comparative Example 4

Stepwise Salt Elution and Separation of Aggregate Under Acidic Conditions of Linked Column of Column Packed with Protein A-Immobilized Carrier and Column Packed with Cation Exchange Chromatography Carrier Using, as carrier 5, CM Sepharose Fast Flow (GE Healthcare Biosciences) of a cation exchange chromatography carrier having a carboxyl group as a ligand, a column from the same company (ID 0.5 cm×Height 2.5 cm) was charged by these, to prepare a 0.5 mL-volume minicolumn. The minicolumn was jointed directly under a column (ID 0.66 cm×Height 7 cm) (manufactured by Omnifit Ltd.) used for evaluation in Preparation Example 3 of carrier in which the carrier 3 was packed, to prepare a linked column (hereinafter referred to as carrier 6). To the linked column, 10 mg of human polyclonal antibody per 1 mL of column packed with the carrier 3 was loaded under neutral conditions, and an antibody was eluted with an elution buffer having various ionic strengths under acidic conditions (chromatography condition 6 for separation of aggregate).

Each eluate was analyzed by gel filtration chromatography, and the protein content and yield (Yield) were found from the protein peak area value of each elution fraction (fraction), and the ratio of a monomeric substance (monomer) and an aggregate (polymer) and the like was further found from the protein peak analysis, to calculate monomeric substance content (Monomer content) and monomeric substance yield (Monomer Yield). At this time, the total sum of the area values of the elution fractions from carrier 3 of Comparative Example 3 was regarded as 100%, and each of elution fractions was evaluated. Moreover, in order to prevent aggregate formation in the elution fraction from the affinity separation matrix, arginine was added to each eluate so that the final concentration became 0.05 M or more, and the pH of each eluate was adjusted to 5 to 6 using a sodium phosphate solution of pH 5. The mixture was subjected to gel filtration chromatography. Moreover, each chromatography condition is shown below. Additionally, gel filtration chromatography was evaluated in the same manner as in Comparative Example 1.

Chromatography Condition 6 for Separation of Aggregate (Acidic pH, Stepwise Salt Elution)

column: ID 0.66 cm×Height 7 cm (manufactured by Omnifit Ltd.) and ID 0.5 cm×Height 2.5 cm (manufactured by GE healthcare bioscience)
flow rate: 0.4 mL/min (contact time: 6 minutes)
polyclonal antibody (IgG): gamma globulin NICHIYAKU (NIHON PHARMACEUTICAL CO., LTD.)
loading solution: 2.5 mg-IgG/mL (PBS: Dulbecco Nissui)
equilibrating solution: PBS (pH 7.4) (3CV)
loading solution: 9.6 mL
washing solution after loading: PBS (pH 7.4) (5CV)
washing solution before elution: 10 mM Tris/HCl (pH7) (5CV)
eluate 1: 10 mM acetic acid (pH 3.5)(8CV)
eluate 2: 10 mM acetic acid containing 25 mM sodium chloride (pH 3.5) (8CV)
eluate 3: 10 mM acetic acid containing 250 mM sodium chloride (pH 3.5) (8CV)
regeneration solution: 0.1 M acetic acid (4CV)
CIP solution: 0.1 M sodium hydroxide, 1 M sodium chloride (4CV)
neutralizing and re-equilibrating solution: PBS (pH 7.4)

The results of evaluation of stepwise salt elution and separation characteristic for an aggregate under acidic conditions of a linked column (carrier 6) of a column packed with the carrier 3 and a column packed with the carrier 5 are shown in Table 6.

TABLE 6

| elution fraction | carrier 6 (linked column of column packed with carrier 3 + column packed with carrier 5) | % |
| --- | --- | --- |
| eluate 1(0 mM NaCl) | antibody yield (%) | 28.5 |
| | monomer content (%) | 90.1 |
| | monomer yield (%) | 27.2 |
| eluate 2(25 mM NaCl) | antibody yield (%) | 1.6 |
| | monomer content (%) | 100.0 |
| | monomer yield (%) | 1.7 |
| eluate 3(250 mM NaCl) | antibody yield (%) | 11.1 |
| | monomer content (%) | 100.0 |
| | monomer yield (%) | 11.7 |
| eluate 1 + eluate 2 + eluate 3 | antibody yield (%) | 41.1 |
| | monomer content (%) | 91.6 |
| | monomer yield (%) | 40.6 |

According to the results of Table 6, not only the column in which a column packed with the protein A-immobilized carrier (carrier 3) and a column packed with the cation exchange chromatography carrier (carrier 5) are linked in series has low monomer selectivity, but also the recovery rate of entire antibodies did not reach even 50%, even at pH 3.5 and increasing the ionic strength to 250 mM [elution fraction in Table 6: eluate 1+2+3]. On the contrary, as shown in Table 4, the carrier 4 shown in Example 2 of the mixed mode antibody affinity separation matrix of the present invention can accomplish high monomer selectivity and high recovery rate [elution fraction in Table 4: eluate 1 (0 mM NaCl)+eluate 2 (25 mM NaCl)]. According to these results, it is important for a mixed mode antibody affinity separation matrix that a protein A ligand and a cation exchange group are present in proximity on a single carrier, and that high recovery rate and high monomer selectivity can be accomplished by concerted functions of the protein A ligand and the cation exchange group in the vicinity.

As described above, by the present invention, a carrier of a novel separation mode which can improve the monomeric substance (monomer) content at a high recovery rate by concerted actions of a protein A ligand and a cation exchange group in one chromatography step as a mixed mode antibody affinity separation matrix, and a method for using the same are provided. Also, contribution to efficient purification of an antibody can be expected.

INDUSTRIAL APPLICABILITY

The mixed mode antibody affinity separation matrix of the present invention is useful for improving the purity of an antibody in a first chromatography step in a process of purifying an antibody or an Fc-containing target molecule, and can be utilized in research and development and production of an antibody preparation.

The invention claimed is:

1. A method for purifying a target molecule comprising the steps of
   applying a solution comprising the target molecule on a column packed with a mixed mode antibody affinity separation matrix comprising an antibody affinity ligand and a cation exchange group on a single separation matrix to adsorb the target molecule on the mixed mode antibody affinity separation matrix,
   passing a buffer solution through the column to wash the column, and
   passing an elution buffer through the column to elute the target molecule,
   wherein both the antibody affinity ligand and the cation exchange group are immobilized to the separation matrix via a covalent bond,
   the cation exchange group is a ligand comprising at least one member selected from the group consisting of a carboxyl group and a sulfate group, and
   the dynamic binding capacity of the cation exchange group under the condition of elution pH for the target molecule is not more than two times that of the dynamic binding capacity of the antibody affinity ligand under the condition of neutral pH.

2. The method according to claim 1, wherein the elution pH of the target molecule is 6 or less.

3. The method according to claim 1, wherein the elution pH of the target molecule is 2 or more.

4. The method according to claim 1, wherein the target molecule is immunoglobulin G, immunoglobulin G derivative, or Fc-containing molecule.

\* \* \* \* \*